（12）United States Patent
Ogura et al.

(10) Patent No.: US 9,595,415 B2
(45) Date of Patent: Mar. 14, 2017

(54) X-RAY GENERATOR AND X-RAY IMAGING APPARATUS

(75) Inventors: Takao Ogura, Yokohama (JP); Yoshihiro Yanagisawa, Fujisawa (JP); Miki Tamura, Kawasaki (JP); Ichiro Nomura, Atsugi (JP); Tamayo Hiroki, Zama (JP); Shigeki Matsutani, Sagamihara (JP); Kazuyuki Ueda, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 173 days.

(21) Appl. No.: 14/241,426

(22) PCT Filed: Aug. 29, 2012

(86) PCT No.: PCT/JP2012/072522
§ 371 (c)(1),
(2), (4) Date: Feb. 26, 2014

(87) PCT Pub. No.: WO2013/032019
PCT Pub. Date: Mar. 7, 2013

(65) Prior Publication Data
US 2014/0362973 A1   Dec. 11, 2014

(30) Foreign Application Priority Data
Aug. 31, 2011   (JP) .................................. 2011-189112

(51) Int. Cl.
*H01J 37/02*   (2006.01)
*H01J 35/08*   (2006.01)
(Continued)

(52) U.S. Cl.
CPC .............. *H01J 35/08* (2013.01); *G01N 23/04* (2013.01); *H01J 35/16* (2013.01);
(Continued)

(58) Field of Classification Search
CPC ........... H01J 2235/087; H01J 2235/186; H01J 35/32; H01J 2235/168; H01J 35/02; H01J 35/16; H01J 35/08; G01N 23/04
(Continued)

(56) References Cited

U.S. PATENT DOCUMENTS 3,840,748 A * 10/1974 Braunlich ............... H01J 27/26
250/423 R
4,159,437 A * 6/1979 Sahores .................. H01J 35/18
378/140
(Continued)

FOREIGN PATENT DOCUMENTS

CN   1252618 A   5/2000
CN   1971834 A   5/2007
(Continued)

OTHER PUBLICATIONS

Filter Transmission, Dec. 6, 2012, Reterieved from the Internet: URL: http: //henke.1b1.gov/optical_constants/filter2.html.
(Continued)

*Primary Examiner* — Wyatt Stoffa
(74) *Attorney, Agent, or Firm* — Canon USA, Inc. I.P. Division

(57) ABSTRACT

Provided is an X-ray generator including an electron passage in an electron-passage forming member; and a target on an insulative substrate. The transmission X-ray generator irradiates the target with electrons that have passed through the electron passage to generate X-rays. The target is provided at a central region of the substrate; the electron passage accommodates a secondary-X-ray generating section that generates X-rays by irradiation with electrons reflected from the target; the secondary-X-ray generating section and the target are disposed so that both of X-rays generated by direct irradiation of the target with the electrons and X-rays generated by irradiation of the secondary-X-ray generating
(Continued)

section with the electrons reflected from the target are radiated to the outside; and at least part of the peripheral region of the substrate has higher transmittance for the X-rays generated at the secondary-X-ray generating section than the central region of the substrate.

16 Claims, 14 Drawing Sheets

(51) Int. Cl.
*G01N 23/04* (2006.01)
*H01J 35/16* (2006.01)

(52) U.S. Cl.
CPC ... *H01J 2235/087* (2013.01); *H01J 2235/168* (2013.01); *H01J 2235/186* (2013.01)

(58) Field of Classification Search
USPC .......................................... 378/62, 121, 124
See application file for complete search history.

(56) References Cited

U.S. PATENT DOCUMENTS

| | | | |
|---|---|---|---|
| 6,151,384 A | 11/2000 | Reed et al. | |
| 6,252,936 B1* | 6/2001 | Smit | H01J 35/08 378/141 |
| 6,661,876 B2* | 12/2003 | Turner | G01N 23/223 313/553 |
| 7,130,379 B2* | 10/2006 | Hamann | H01J 35/08 378/119 |
| 7,233,647 B2* | 6/2007 | Turner | G21K 1/10 378/140 |
| 7,382,862 B2* | 6/2008 | Bard | H01J 35/14 378/121 |
| 7,783,011 B2* | 8/2010 | Ito | H01J 9/26 378/121 |
| 2003/0021377 A1* | 1/2003 | Turner | G01N 23/223 378/102 |
| 2004/0076260 A1* | 4/2004 | Charles, Jr. | H01J 35/08 378/124 |
| 2005/0207537 A1* | 9/2005 | Ukita | H01J 35/28 378/125 |
| 2005/0276382 A1 | 12/2005 | Lesiak et al. | |
| 2007/0076849 A1* | 4/2007 | Bard | H01J 35/14 378/121 |
| 2009/0028297 A1* | 1/2009 | Matoba | H01J 35/08 378/140 |
| 2009/0041196 A1 | 2/2009 | Matoba et al. | |
| 2009/0279669 A1 | 11/2009 | Allen et al. | |
| 2011/0058655 A1* | 3/2011 | Okumura | H01J 35/12 378/143 |
| 2011/0085641 A1* | 4/2011 | Okunuki | H01J 35/065 378/62 |
| 2012/0051496 A1* | 3/2012 | Wang | H01J 35/08 378/4 |
| 2012/0140895 A1* | 6/2012 | Okunuki | H01J 35/065 378/122 |
| 2012/0318987 A1* | 12/2012 | Miyazaki | H01J 35/08 250/358.1 |
| 2013/0266119 A1* | 10/2013 | Taniguchi | H01J 35/14 378/62 |
| 2014/0211919 A1* | 7/2014 | Ogura | H01J 35/08 378/62 |
| 2014/0362972 A1* | 12/2014 | Ogura | H01J 35/14 378/62 |
| 2014/0362973 A1* | 12/2014 | Ogura | H01J 35/08 378/62 |
| 2014/0369469 A1* | 12/2014 | Ogura | H01J 35/08 378/62 |
| 2015/0117616 A1* | 4/2015 | Ishii | H01J 35/08 378/137 |

FOREIGN PATENT DOCUMENTS

| | | |
|---|---|---|
| CN | 101355002 A | 1/2009 |
| EP | 777255 A1 | 6/1997 |
| EP | 2293318 A1 | 3/2011 |
| GB | 2473137 A | 3/2011 |
| JP | 2-297850 A | 12/1990 |
| JP | 09171788 A | 6/1997 |
| JP | 11144653 A | 5/1999 |
| JP | 2002352754 A | 12/2002 |
| JP | 2005-523558 A | 8/2005 |
| JP | 2006-236656 A | 9/2006 |
| JP | 2009-031167 A | 2/2009 |
| JP | 2009-031168 A | 2/2009 |
| JP | 2009-189507 A | 8/2009 |
| JP | 2009-205992 A | 9/2009 |
| JP | 2010-027302 A | 2/2010 |
| JP | 2011-071101 A | 4/2011 |
| JP | 2011-077027 A | 4/2011 |
| WO | 2007/100105 A1 | 9/2007 |
| WO | 2008/156361 A2 | 12/2008 |
| WO | 2011/105035 A2 | 9/2011 |

OTHER PUBLICATIONS

Jensen, et al, "Improvements in Low Power, End-Window, Transmission-Target X-Ray Tubes", vol. 47, 2004, pp. 64-69. (The year of publication for this reference is sufficiently earlier than the effective U.S. filing date and any foreign priority date so that the particular month of publication is not in issue.).
Cornaby, et al, "Simultaneous XRD/XRF With Low-Power X-Ray Tubes", vol. 45, Jan. 1, 2002, pp. 34-40.
International Search Report and Written Opinion for PCT/JP2012/072514 and notification of transmittal of the ISR/WO, dated Dec. 10, 2012.
International Search Report and Written Opinion for PCT/JP2012/072524 and notification of transmittal of the ISR/WO, dated Apr. 18, 2013.
International Search Report and Written Opinion for PCT/JP2012/072515 and notification of transmittal of the ISR/WO, dated Jan. 2, 2013.

* cited by examiner

X-RAY GENERATOR AND X-RAY IMAGING APPARATUS

TECHNICAL FIELD

The present invention relates to a transmission X-ray generator applicable to X-ray imaging for diagnosis in the medical field, nondestructive inspection in the field of industrial equipment, and so on, and to an X-ray imaging apparatus including the same.

BACKGROUND ART

The X-ray generation efficiency of transmission X-ray generators that irradiate a transmission target with electrons to generate X-rays is generally extremely low. When accelerating electrons to high energy and irradiating the target to generate X-rays, only about 1% or less of the energy of the colliding electrons becomes X-rays, and the remaining about 99% or more becomes heat. Thus, an increase in X-ray generation efficiency is required. When electrons collide with the target, reflected electrons are generated. It is known that the reflected electrons do not contribute to generation of X-rays for use.

PTL 1 discloses an X-ray tube whose X-ray generation efficiency is increased by disposing an anode member having a conical channel whose opening diameter is decreased from an electron source toward a target between the electron source and the target and by elastically scattering the electrons on the channel surface to let the electrons incident on the target.

PTL 2 discloses a transmissive X-ray target in which target metal is formed on a ceramic or glass X-ray transmission window substrate.

CITATION LIST

Patent Literature

PTL 1 Japanese Patent Laid-Open No. 9-171788
PTL 2 Japanese Patent Laid-Open No. 2002-352754

SUMMARY OF INVENTION

Technical Problem

The technique described in PTL 1 provides a micro-focus X-ray tube in which the number of electrons incident on the target is substantially increased. However, the X-ray generation efficiency of the X-ray tube is not always sufficient to use it for an X-ray imaging apparatus. The technique described in PTL 2 can prevent charging-up of the target but does not increase the X-ray generation efficiency.

Solution to Problem

To solve the above problems, the present invention provides an X-ray generator including an electron passage formed by surrounding the periphery thereof with an electron-passage forming member; and a target provided on an insulative substrate and irradiated with electrons that have passed through the electron passage to generate X-rays, wherein the target is provided at a central region of the substrate; the electron passage accommodates a secondary-X-ray generating section that generates X-rays by irradiation with electrons reflected from the target; the secondary-X-ray generating section and the target are disposed so that both of X-rays generated by direct irradiation of the target with the electrons and X-rays generated by irradiation of the secondary-X-ray generating section with the electrons reflected from the target are radiated to the outside; and at least part of the peripheral region of the substrate, the peripheral region being not covered by the target, has higher transmittance for the X-rays generated at the secondary-X-ray generating section than the central region of the substrate, the central region being covered with the target.

Advantageous Effects of Invention

According to some embodiments of the present invention, in addition to X-rays generated at a transmission target, X-rays generated due to reflected electrons generated at the transmission target can be efficiently extracted to the outside. Thus, the X-ray generation efficiency can be improved, and hence a high-output transmission X-ray generator suitable for X-ray imaging can be provided.

DESCRIPTION OF EMBODIMENTS

A target unit of according to embodiments of the present invention includes a target support substrate (hereinafter referred to as a substrate) 3 and a transmission target (hereinafter referred to as a target) 1 placed on the substrate 3.

First Embodiment

Figure 1A:
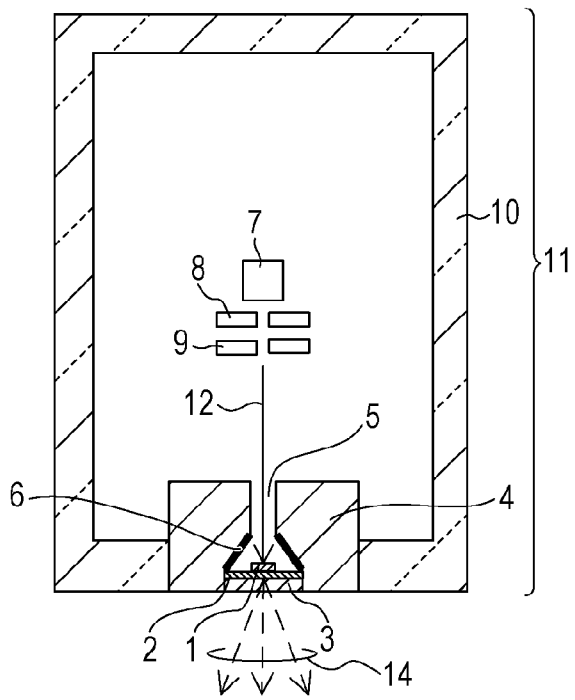
FIG. 1A is a schematic diagram showing the configuration of an X-ray tube according to a first embodiment of the present invention.
Figure 1B:
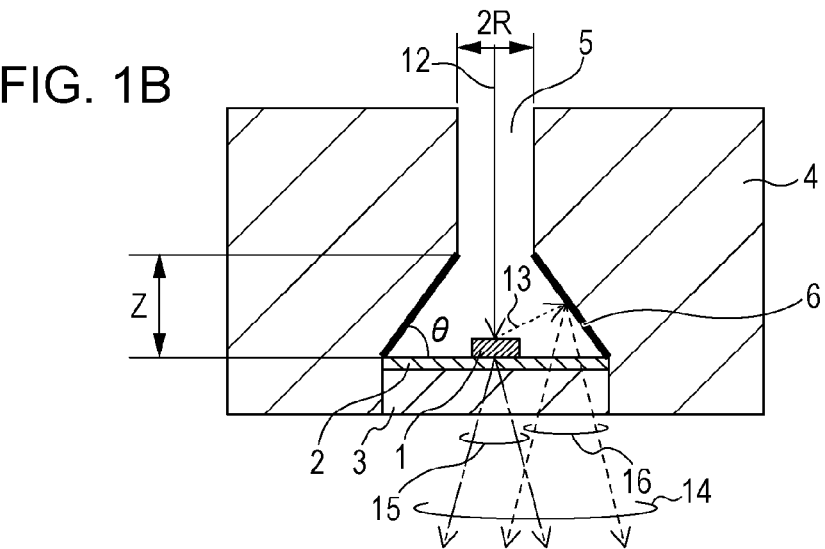
FIG. 1B is an enlarged view of the vicinity of a target.
Figure 1C:
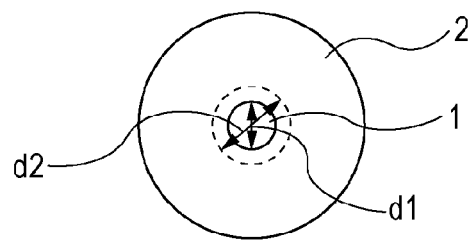
FIG. 1C is a plan view of a target unit, as viewed from the target side.

FIG. 1A is a schematic diagram of a transmission X-ray generating tube (hereinafter referred to as an X-ray tube) 11 of a first embodiment of the present invention. FIG. 1B is an enlarged view of the vicinity of the target 1 in FIG. 1A. FIG. 1C is a plan view of the target unit in FIG. 1A, as viewed from the target side.

A vacuum container 10 is used to maintain the interior of the X-ray tube 11 under vacuum and is formed of a glass or ceramic material or the like. The degree of vacuum in the vacuum container 10 is preferably about $10^{-4}$ to $10^{-8}$ Pa. The vacuum container 10 has an opening, to which an electron-passage forming member 4 having an electron passage 5 is joined. The substrate 3 is joined to the inner wall surface of the electron passage 5 to tightly seal the vacuum container 10.

An electron emission source 7 is disposed in the vacuum container 10 so as to face the target 1. The electron emission source 7 may be a tungsten filament, a hot cathode, such as an impregnated cathode, or a cold cathode, such as a carbon nanotube. Electrons 12 emitted from the electron emission source 7 enter at an end of the electron passage 5 formed in the electron-passage forming member 4, pass through the electron passage 5, and irradiate the target 1 provided at the other end of the electron passage 5 to generate X-rays 14. A voltage Va applied between the electron emission source 7 and the target 1 is about 40 kV to 150 kV, although depending on the application of the X-rays. A collimator for limiting the radiation field of X-rays may be disposed outside the X-ray tube 11.

The target 1 is disposed in the central region of the surface of the substrate 3 adjacent to the electron emission source 7 on which an electrically conducting layer 2 is provided. The electron-passage forming member 4 is disposed between the target 1 and the electron emission source 7, in which the electron passage 5 whose both ends are open is formed by surrounding the periphery thereof with the electron-passage forming member 4. The cross-sectional area of at least the end of the electron passage 5 adjacent to the target 1 continuously increases as compared with the opposite side. The inner wall surface of the increased-cross-sectional-area region of the electron passage 5 serves as a secondary-X-ray generating section 6. The secondary-X-ray generating section 6 is hereinafter referred to as a secondary-X-ray generation surface because it is shaped like a surface. It is sufficient that at least part of the inner wall surface of the increased-cross-sectional-area region of the electron passage 5 serve as the secondary-X-ray generation surface 6. The secondary-X-ray generation surface 6 may either be formed as part of the inner wall surface of the electron passage 5 or be formed, in the electron passage 5, of a member different from that of the electron passage 5.

With the above configuration, the electrons 12 emitted from the electron emission source 7 pass through the electron passage 5 and collide with the target 1. Since the accelerated electrons 12 collide with the region of the target 1 irradiated with the electrons, X-rays 15 are generated. The generated X-rays 15 pass through the electrically conducting layer 2 and the substrate 3 and are radiated outside the X-ray tube 11. Although part of the X-rays 15 is attenuated due to self-absorption of the target 1 and also by the substrate 3 serving also as an X-ray transmission window, the degree of attenuation is low, and is substantially permissible. Preferably, the diameter d1 of the target 1 shown in FIGS. 1B and 1C is substantially equal to the diameter of the cross section of the electrons 12 (electron beam). Even if there is a slight difference therebetween, there is no substantial difference although the effect is limited.

When the electrons 12 collide with the target 1, reflected electrons 13 are generated, as well as the X-rays 15. The reflected electrons 13 generated at the target 1 collide with the secondary-X-ray generation surface 6 to generate X-rays 16. At least part of the generated X-rays 16 (hereinafter also referred to as secondary X-rays) passes through the substrate 3 and is radiated outside the X-ray tube 11.

The reflected electrons 13 amount to 20% to 60% of the electrons that have collided with the target 1, although depending on the material, surface state, and so on of the target 1. The acceleration voltage when the reflected electrons 13 collide with the secondary-X-ray generation surface 6 is lower than the acceleration voltage of the electrons 12 emitted by the electron emission source 7. The degree also depends on the material and surface state of the target 1, the direction of emission, and so on. Therefore, the energy of the secondary X-rays (X-rays 16) is lower than the energy of the X-rays 15. Although the secondary X-rays are radiated in all directions from the secondary-X-ray generation surface 6 with which the reflected electrons 13 collide, using a material that can block the X-rays as the electron-passage forming member 4 allows most of the secondary X-rays 16 radiated backwards to be blocked by the inner wall of the electron passage 5. The secondary X-rays 16 radiated forwards can be used for imaging as are the X-rays 15 because they are radiated through the target 1.

Figure 2A:
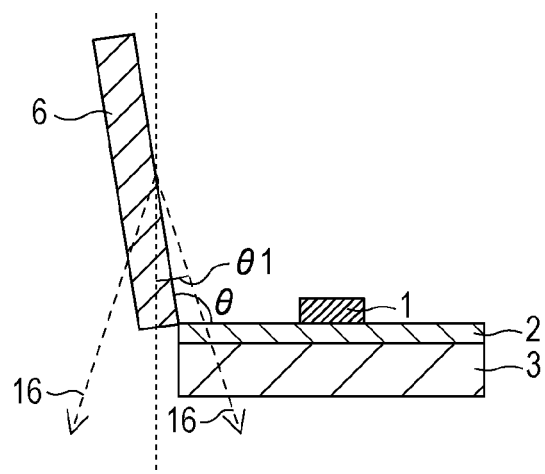
FIGS. 2A to 2C are schematic diagrams showing the relationship between an angle θ formed by a secondary-X-ray generation surface and the target and the radiating direction of X-rays.
Figure 2B:
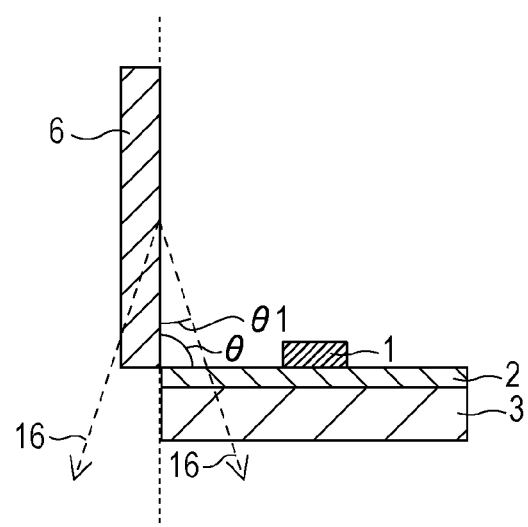
Figure 2C:
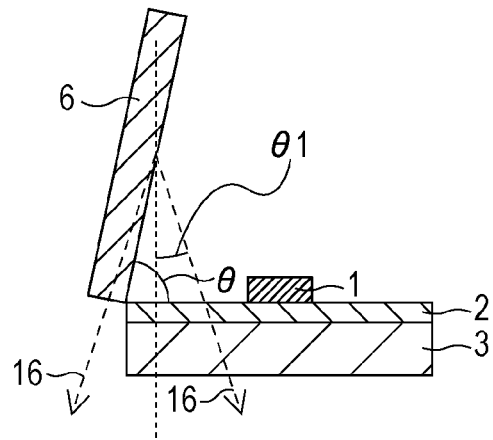

Next, a preferable range of an angle θ that is formed by the secondary-X-ray generation surface 6 with the target 1 will be described. FIGS. 2A to 2C show the X-rays 16 generated at the secondary-X-ray generation surface 6 after the reflected electrons 13 collide with the secondary-X-ray generation surface 6, showing the positional relationship between the X-rays 16 generated at any angle θ1 with respect to a perpendicular line of the target 1 and the components. FIG. 2A shows a case where θ>90°, FIG. 2B shows a case where θ=90°, and FIG. 2C shows a case where θ<90°. If θ>90°, as in FIG. 2A, much of the generated X-rays 16 is absorbed through the secondary-X-ray generation surface 6, and thus only a little is radiated to the outside. If θ=90°, as in FIG. 2B, about half of the generated X-rays 16 is absorbed in the secondary-X-ray generation surface 6. If θ<90°, as in FIG. 2C, much of the generated X-rays 16 (at least about half or more) is radiated to the outside without being absorbed. Thus, setting at θ<90°, that is, forming the electron passage 5 whose end adjacent to the target 1 is increased in cross-sectional area as compared with the end opposite the target 1 reduces the proportion of the generated X-rays 16 absorbed in the secondary-X-ray generation surface 6, thus increasing the amount of X-rays 16 extracted.

Figure 3A:
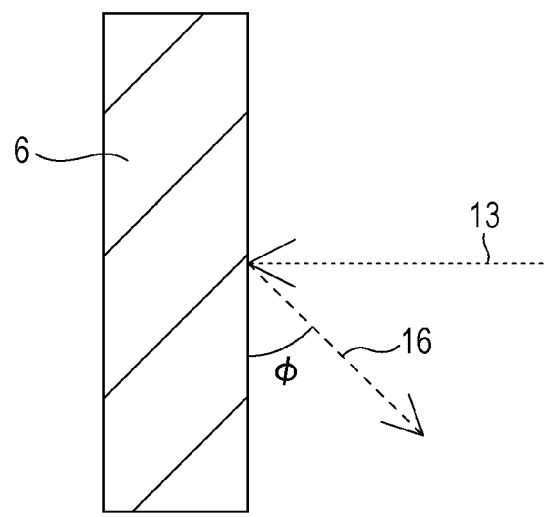
FIGS. 3A and 3B are diagrams explaining the exit angle dependency of X-ray intensity.
Figure 3B:
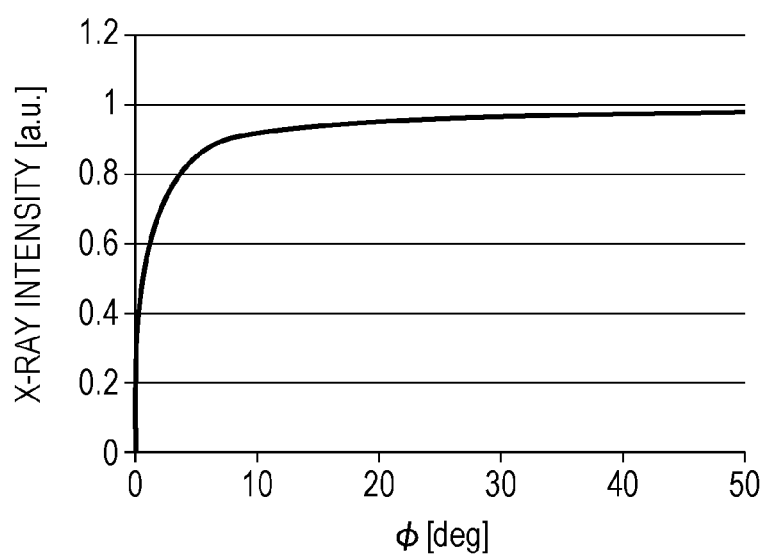

A preferable range of the angle θ can also be set in consideration of the exit angle dependency of the X-ray intensity. FIGS. 3A and 3B are diagrams explaining the exit angle dependency of the X-ray intensity. FIG. 3A shows a state in which the reflected electrons 13 are incident on the secondary-X-ray generation surface 6, and the generated X-rays 16 exit at an exit angle φ, and FIG. 3B shows the relationship between the X-ray exit angle φ in FIG. 3A and X-ray intensity. Since the reflected electrons 13 accelerated to 10 kV to 200 kV enter about a few μm inside the secondary-X-ray generation surface 6 without heavily depending on the incident angle, much of the X-rays 16 is also generated about a few μm inside the secondary-X-ray generation surface 6. The generated X-rays 16 are radiated at various angles. If the X-ray exit angle φ in FIG. 3A is small, the distance of passage of the X-rays 16 in the secondary-X-ray generation surface 6 is long. Therefore, for example, if φ<5°, the X-ray intensity rapidly decreases as φ decreases, as shown in FIG. 3B. Accordingly, if the lower limit of the exit angle φ is set to $φ_0$ in consideration of the exit angle dependency of the X-ray intensity, a preferable range of the angle θ is θ<90−$φ_0$, in addition to the above-described preferable range. Referring to FIG. 3B, if $φ_0$ is set to 5°, θ<85° is given. The lower limit of θ is 10°<θ in consideration of a threshold value for causing the electrons 13 reflected by the target 1 to collide with the inner wall surface with efficiency. Thus, a preferable range of the angle θ is 10°<θ<85°.

Figure 4A:
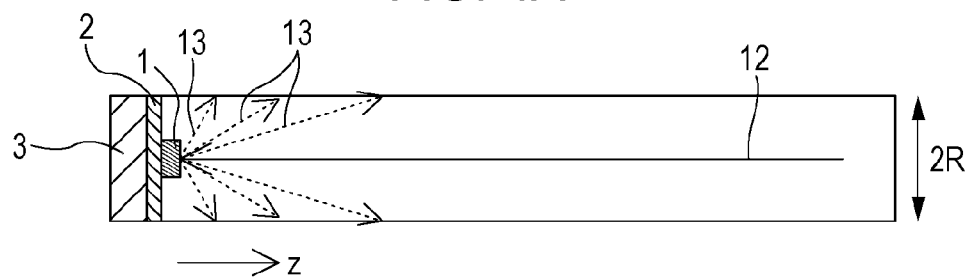
FIGS. 4A to 4C are diagrams explaining the collision density distribution of the reflected electrons.
Figure 4B:
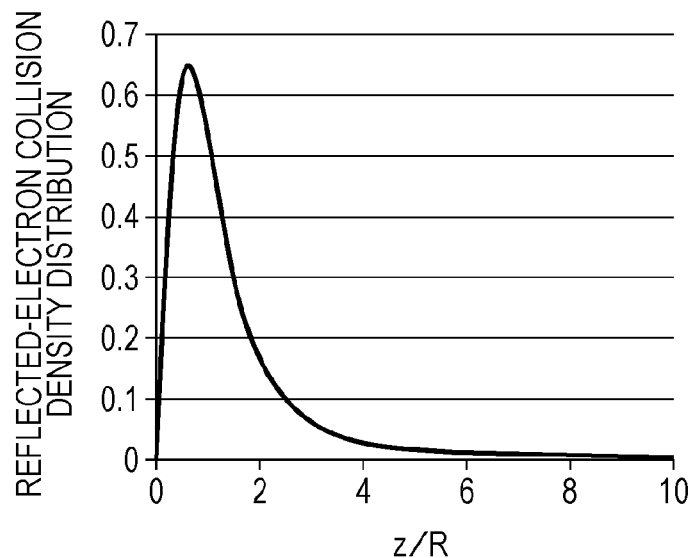
Figure 4C:
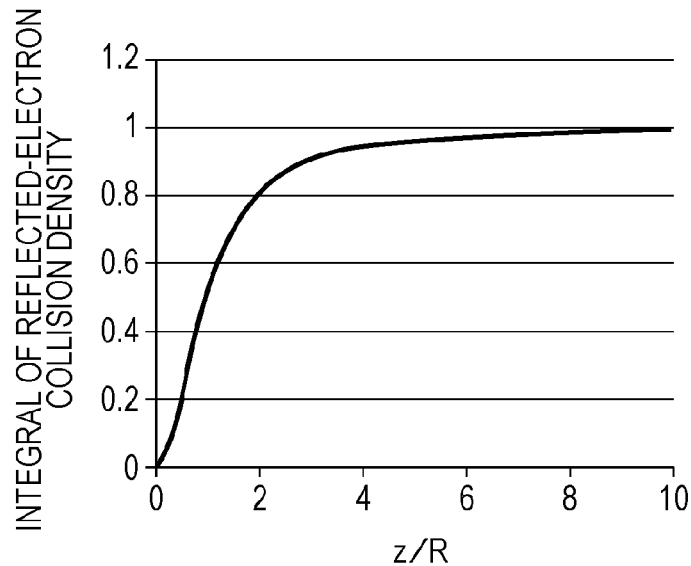

Next, a preferable range of a region where the secondary-X-ray generation surface 6 is formed will be described with reference to FIGS. 4A to 4C. Here, a preferable range of the distance Z between the target 1 and the end of the secondary-X-ray generation surface 6 remote from the target 1 (a secondary-X-ray-generation-surface formation distance) will be described. The preferable range of the distance Z can be set in consideration of the distribution of the density of the reflected electrons 13 generated at the target 1 which have reached the periphery. FIGS. 4A to 4C are diagrams explaining the collision density distribution of the reflected electrons 13. FIG. 4A is a schematic diagram for use in calculation; FIG. 4B is a graph showing the collision density distribution of the reflected electrons 13 generated due to the incident electrons 12; and FIG. 4C is a diagram showing the integral of the collision density of the reflected electrons 13. In FIG. 4A, if the width of the opening perpendicular to the direction z (coordinate) is 2R, most of the reflected electrons 13, about 80% of all, reaches the peripheral surface where the distance (coordinate) z is 2R or less. If the distance z is 4R or less, about 95% of all reaches the peripheral surface. Accordingly, if the opening width of the electron passage 4 is 2R, preferably, the secondary-X-ray generation surface 5 is formed at a region where the distance z is at least 2R or less, more preferably, 4R or less. If the distance z is 20R, the collision density of the reflected electrons 13 becomes substantially zero. Accordingly, preferably, the opening width 2R of the electron-passage forming member 3 and the formation distance (height) Z of the secondary-X-ray generation surface satisfy the relation, 2≤Z/R≤20. More preferably, they satisfy the relation, 4≤Z/R≤20.

In FIG. 1B, although the secondary-X-ray generation surface 6 is formed over the entire surface of the inner wall of the increased-cross-sectional-area region of the electron passage 5, the secondary-X-ray generation surface 6 does not necessarily need to be formed over the entire surface of the inner wall of the increased-cross-sectional region of the electron passage 5. The secondary-X-ray generation surface 6 may be formed on a region including the range of the preferable distance Z.

The secondary-X-ray generating section 6 and the target 1 are disposed so that both the X-rays 15 generated when the electrons 12 are radiated directly onto the target 1 and the X-rays 16 generated when electrons 13 reflected by the target 1 irradiates the secondary-X-ray generating section 6 are radiated to the outside. The secondary-X-ray generating section 6 may be disposed over the target 1 so as to cover the surface thereof irradiated with the electrons 12. The secondary-X-ray generation surface 6 may either be formed as part of the inner wall surface of the electron passage 5 or be formed, in the electron passage 5, of a member different from that of the electron passage 5.

The target 1 may be formed of a material having a high melting point and high X-ray generation efficiency. Suitable examples of such a material are metals with atomic numbers equal to or greater than 26, such as tungsten, tantalum, and molybdenum. A preferable thickness of the target 1 is about several μm to several tens μm to reduce absorption when the generated X-rays pass through the target 1.

If the electrically conducting layer 2 is provided merely to prevent charging-up of the target unit, there is no limitation to the kind and thickness of the material provided that it has electrical conductivity. However, since the present invention is made to provide the electrically conducting layer 2 with the function of extracting the X-rays generated at the secondary-X-ray generation surface 6 to the outside, the kind and thickness of the material have some influence. Generation of X-rays 16 at the secondary-X-ray generation surface 6, an extraction method for the X-rays 16, and the kind of the material will be described in detail below.

A suitable material for the substrate 3 has a sufficient strength to support the target 1 and absorbs little X-rays 15 and 16 generated at the target 1 and the secondary-X-ray generation surface 6. The material may have high thermal conductivity so as to radiate heat generated in the target 1, such as diamond, silicon nitride, aluminum, and nitride. An appropriate thickness of the substrate 3 is about 0.1 mm to several mm. An insulative material may also be used.

The secondary-X-ray generation surface 6 may be formed of a material having a high melting point and high X-ray generation efficiency. Suitable examples of such a material are metals with atomic numbers equal to or greater than 26, such as tungsten, tantalum, and molybdenum. A preferable thickness of the secondary-X-ray generation surface 6 is larger than the intrusion length of electrons, preferably, several μm or more. The material of the secondary-X-ray generation surface 6 may be the same as of that of the target 1. This is because the X-rays 15 generated when electrons 12 emitted from the electron emitting portion of the electron emission source 7 collide directly with the target 1 and the X-rays 16 generated when the electrons 13 reflected from the target 1 collide with the secondary-X-ray generation surface 6 have the same characteristics.

A suitable material for the electron-passage forming member 4 can block X-rays. The electron-passage forming member 4 may be formed of the same material as that of the secondary-X-ray generation surface 6. In this case, the surface of the electron-passage forming member 4 serves as the secondary-X-ray generation surface 6. The material of the electron-passage forming member 4 may differ from that of the secondary-X-ray generation surface 6. The material of the electron-passage forming member 4 may have high thermal conductivity so as to quickly radiate heat generated in the secondary-X-ray generation surface 6, for example, tungsten, tantalum, molybdenum, copper, silver, gold, and nickel.

The electron passage 5 serves, at the side closer to the electron emission source 7 than the target 1, as a passage for guiding the electrons 12 to the electron beam irradiation region (X-ray generation region) of the target 1. Using a material that can block X-rays as the electron-passage forming member 4 allows most of the X-rays radiated from the target 1 toward the electron emission source 7 (rearwards) to be blocked by the inner wall of the electron passage 5. An X-ray passage can be provided opposite the electron emission source 7 with respect to the target 1. Using a material that can block X-rays for the X-ray passage allows unnecessary X-rays of the X-rays radiated from the target 1 toward the opposite to the electron emission source 7 (forwards) to be blocked by the inner wall of the X-ray passage. The electron passage 5 and the X-ray passage can be integrally formed of the same material. The shapes of the electron passage 5 and the X-ray passage may be circular or may be in any form, such as rectangular and elliptical, as viewed from the electron emission source 7 side.

The electron-passage forming member 4 and the target unit can be joined together by brazing or the like. For brazing, it is important to maintain the interior of the vacuum container 10 under vacuum. The material of brazing can be selected as appropriate depending on the material, heatproof temperature, and so on of the electron-passage forming member 4.

As shown in FIG. 1B, the target unit has a configuration in which the electrically conducting layer 2 is provided on the substrate, and the target 1 is placed on the central region of the electrically conducting layer 2. In FIGS. 1B and 1C, reference sign d1 denotes the diameter of the target 1, and d2 denotes the inside diameter of the electron incident end of the electron passage 5. The target unit and the electron-passage forming member 4 are joined together with a brazing material (not shown), so that the interior of the vacuum container 10 is maintained under vacuum. The substrate 3 and the electrically conducting layer 2 are also brazed to the electron-passage forming member 4.

When the secondary X-rays (X-rays 16) pass through the target unit, some of them passes through the two layers, that is, the electrically conducting layer 2 and substrate 3, and some passes through the three layers, that is, the target 1, the electrically conducting layer 2, and the substrate 3. The material and thickness of the target 1 should be optimized depending on the use conditions to generate X-rays efficiently when the electrons 12 collide therewith. On the other hand, since the electrically conducting layer 2 generates little X-rays when the electrons 12 collides therewith, only electrical conductivity, which is its original function, and X-ray transmissivity may be considered. However, since the energy of the secondary X-rays 16 is smaller than the energy of the X-rays 15, as described above, if the material and thickness of the electrically conducting layer 2 are the same as those of the target 1, the electrically conducting layer 2 absorbs much X-rays, and hence a sufficient amount of secondary X-rays 16 cannot be extracted. Considering only the X-ray transmissivity, it is most desirable to eliminate the electrically conducting layer 2; however, considering prevention of the charging-up, described above, a thinnest possible electrically conducting layer 2 is needed.

The material having high X-ray transmissivity for the electrically conducting layer 2 may be a light element, for example, aluminum, titanium, silicon nitride, silicon, and graphite. The electrically conducting layer 2 formed of such an element having a mass smaller than that of the target 1 has only to have electrical conductivity, and preferably has a thickness of about 0.1 nm or larger and 1 μm or less. The material of the electrically conducting layer 2 may be the same as that of the target 1. If the material of the electrically conducting layer 2 is the same as that of the target 1, the electrically conducting layer 2 may be thin enough not to substantially hinder the X-rays from passing therethrough. Even a metal material with an atomic number equal to or greater than 26, which is generally used as the target 1, can be used as the electrically conducting layer 2 because of its high X-ray transmittance provided that it is thin. For example, tungsten with a thickness of about 0.1 nm or more and 0.2 μm or less blocks slight X-rays, and thus it can be employed as, as well as a light element. With such a configuration, for the X-rays (secondary X-rays) 16 generated when the electrons 13 reflected from the target 1 are incident on the inner wall surface of the electron passage 5, the transmittance at the central region of the substrate 3 covered by the target 1 is 30% to 70% of the transmittance at the peripheral region of the substrate 3 which is not covered by the target 1.

In FIG. 1B, although the electrically conducting layer 2 is provided on the substrate 3, and the target 1 is provided on the electrically conducting layer 2, they need not be provided in this order.

In the case of the target unit in which the target 1 is provided on the electrically conducting layer 2, it is preferably that the thickness of the region of the electrically conducting layer 2 covered by the target 1 be 0.1 nm or more and 0.1 μm or less. This range of thickness ensures good linearity and output stability of X-ray radiation. The thickness of the region of the electrically conducting layer 2 other than the region covered by the target 1 may not necessarily be within the above range. If the electrically conducting layer 2 and the target 1 are formed of the same material, the thickness of the region of the electrically conducting layer 2 covered by the target 1 need not be within the above range.

In the case of a target unit in which the electrically conducting layer 2 is provided on the target 1, it is preferable that the thickness of the region of the electrically conducting layer 2 covering the target 1 be 0.1 nm or more and 0.1 μm or less. This range of thickness allows the amount of X-rays 15 generated when the electrons 12 collides directly with the electrically conducting layer 2 to be lower than or equal to an allowable range. The thickness of the region of the electrically conducting layer 2 other than the region covering the target 1 need not be within the above range because electrons 12 do not collide directly with the electrically conducting layer 2. If the electrically conducting layer 2 and the target 1 are formed of the same material, the thickness of the region of the electrically conducting layer 2 covering the target 1 need not be within the above range.

According to this embodiment, the secondary X-rays 16 can be generated at the secondary-X-ray generation surface 6, and the peripheral region of the substrate 3, which is not covered by the target 1, is covered by the electrically conducting layer 2. Thus, the secondary-X-ray transmissivity at the peripheral region is higher than that at the central region. This allows the secondary X-rays 16 generated due to reflected electrons 13 generated at the target 1, in addition to the X-rays 15 generated at the target 1, to be efficiently extracted. This can improve the X-ray generation efficiency.

Modifications of the configuration of the target unit will be described hereinbelow. The target 1, the electrically conducting layer 2, and the substrate 3 can be formed of the materials described above.

Figure 7A:
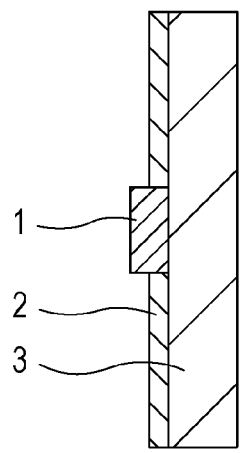
FIG. 7A is a schematic diagram of another target unit according to an embodiment of the present invention.
Figure 7B:
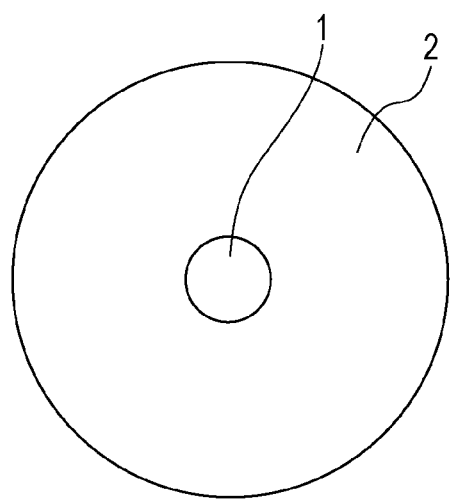
FIG. 7B is a plan view of the target unit in FIG. 7A.

A target unit shown in FIGS. 7A and 7B has a configuration in which the target 1 is provided on the central region of the substrate 3, and the electrically conducting layer 2 is provided on the region other than the central region of the substrate 3. Since the peripheral region of the substrate 3, which is not covered by the target 1 connected to the electrically conducting layer 2, is covered with the electrically conducting layer 2, the secondary-X-ray transmissivity of the peripheral region is higher than that at the central region.

Figure 7C:
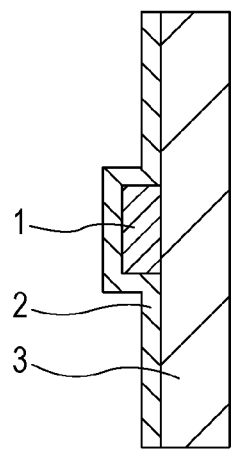
FIG. 7C is a schematic diagram of another target unit according to an embodiment of the present invention.
Figure 7D:
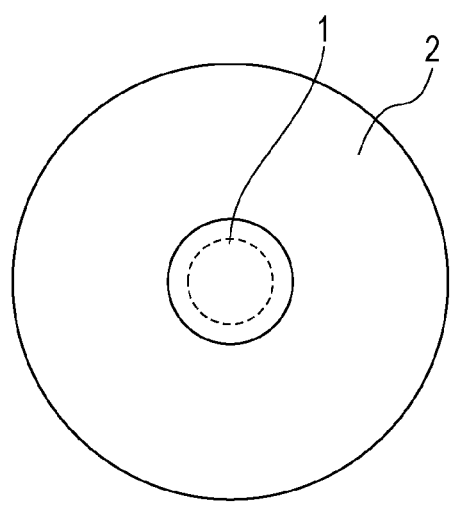
FIG. 7D is a plan view of the target unit in FIG. 7C.

A target unit shown in FIGS. 7C and 7D has a configuration in which the target 1 is provided on the central region of the substrate 3, and the electrically conducting layer 2 is provided on the region other than the central region of the substrate 3 and on the target 1. The target 1 is covered with the electrically conducting layer 2. Since the peripheral region of the substrate 3, which is not covered by the target 1, is covered with the electrically conducting layer 2, the secondary-X-ray transmissivity at the peripheral region is higher than at the central region.

Figure 8A:
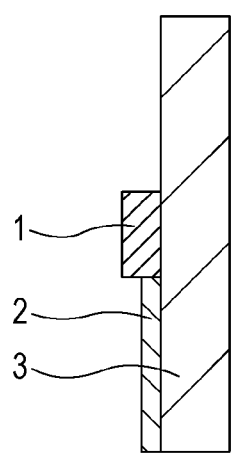
FIG. 8A is a schematic diagram of another target unit according to an embodiment of the present invention.
Figure 8B:
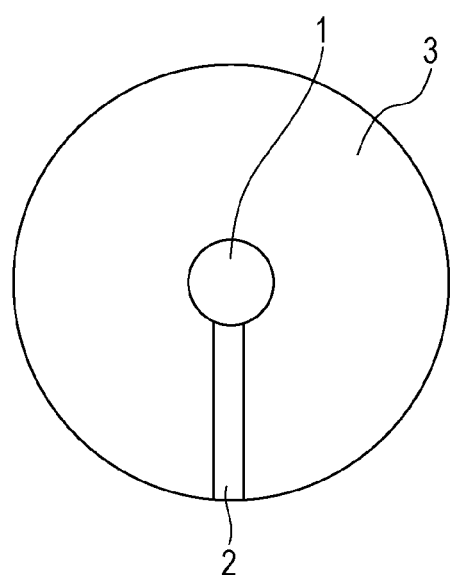
FIG. 8B is a plan view of the target unit in FIG. 8A.

A target unit shown in FIGS. 8A and 8B has a configuration in which the target 1 provided on the central region of the substrate 3, and the electrically conducting layer 2 extending from the central region to the rim is provided at part of the substrate 3 other than the central region. The target 1 is connected to the electrically conducting layer 2. The electrically conducting layer 2 is provide on part of the peripheral region of the substrate 3 which is not covered with the target 1, and the other part of the peripheral region is an exposed surface of the substrate 3. Since only part of the peripheral region of the substrate 3, which is not covered with the target 1, is covered with the electrically conducting layer 2, the secondary-X-ray transmissivity is high at the peripheral region.

Figure 8C:
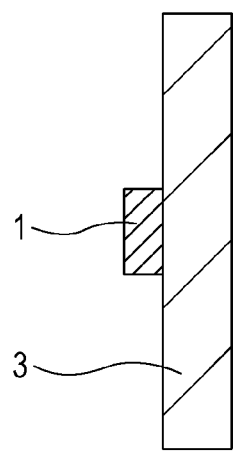
FIG. 8C is a schematic diagram of another target unit according to an embodiment of the present invention.
Figure 8D:
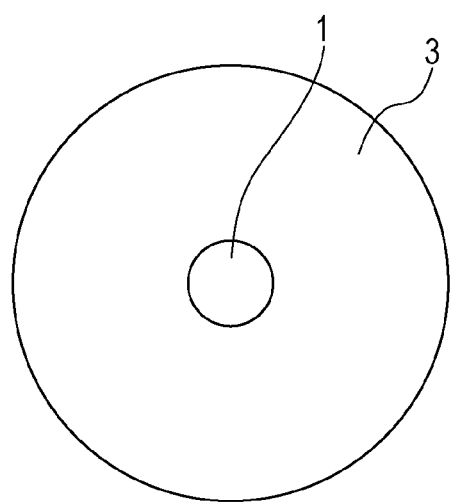
FIG. 8D is a plan view of the target unit in FIG. 8C.

A target unit shown in FIGS. 8C and 8D has a configuration in which the target 1 is provided on the central region of the substrate 3, and the electrically conducting layer 2 is not provided. In this case, the substrate 3 may have slight electrical conductivity. If the electrical conductivity is not sufficient, use conditions or the like may be limited to prevent charging-up. Since the target 1 is provided on the central region of the substrate 3, and the electrically conducting layer 2 is not provided, the secondary-X-ray transmissivity is higher at the peripheral region of the substrate 3, which is not covered with the target 1.

Figure 9A:
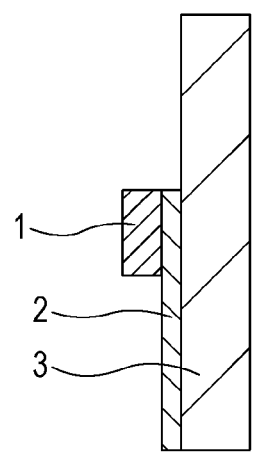
FIG. 9A is a schematic diagram of another target unit according to an embodiment of the present invention.
Figure 9B:
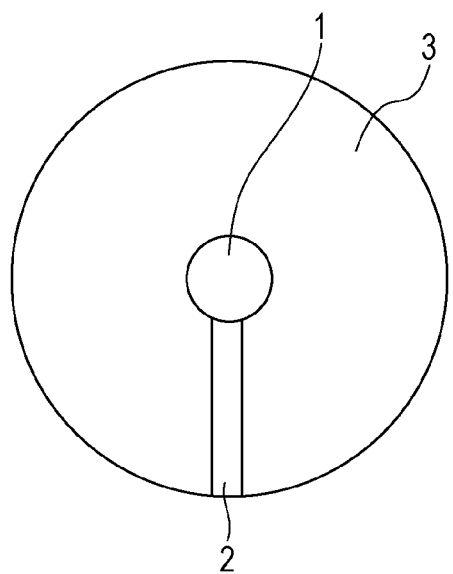
FIG. 9B is a plan view of the target unit in FIG. 9A.

A target unit shown in FIGS. 9A and 9B has a configuration in which the electrically conducting layer 2 is provided on the central region of the substrate 3, and also the electrically conducting layer 2 extending from the central region to the rim is provided on part of the region of the substrate 3 other than the central region. The target 1 is provided on the part of the electrically conducting layer 2 located on the central region of the substrate 3. The electrically conducting layer 2 is provided only on part of the peripheral region of the substrate 3, which is not covered with the target 1, and the other part of the peripheral region is an exposed surface of the substrate 3. Since part of the peripheral region of the substrate 3, which is not covered with the target 1, is covered with the electrically conducting layer 2, the secondary-X-ray transmissivity is high at the peripheral region.

Figure 9C:
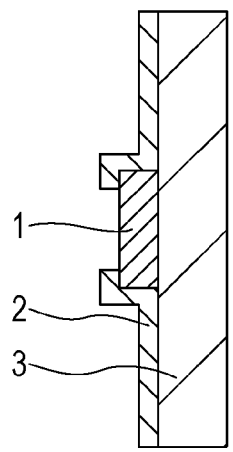
FIG. 9C is a schematic diagram of another target unit according to an embodiment of the present invention.
Figure 9D:
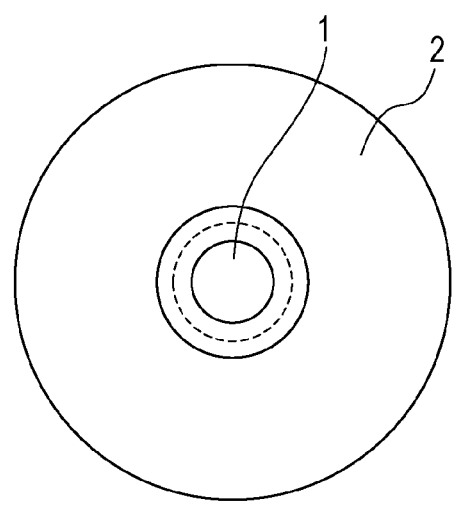
FIG. 9D is a plan view of the target unit in FIG. 9C.

A target unit shown in FIGS. 9C and 9D has a configuration in which the target 1 is provided on the central region of the substrate 3, and the electrically conducting layer 2 is provided on the region of the substrate 3 other than the central region and on the peripheral region of the target 1. Since the peripheral region of the substrate 3, which is not covered with the target 1, is covered with the electrically conducting layer 2, the secondary-X-ray transmissivity is higher at the peripheral region than at the central region.

Figure 9E:
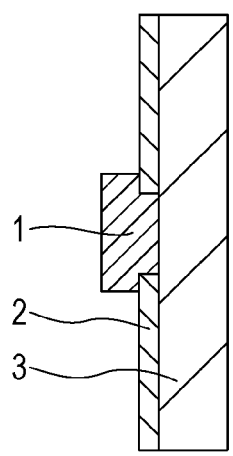
FIG. 9E is a schematic diagram of another target unit according to an embodiment of the present invention.
Figure 9F:
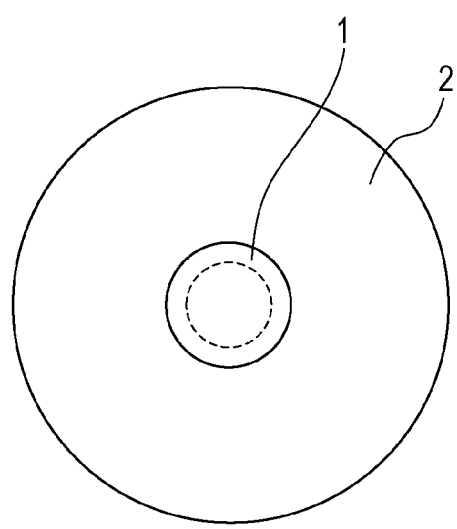
FIG. 9F is a plan view of the target unit in FIG. 9E.

A target unit shown in FIGS. 9E and 9F has a configuration in which the electrically conducting layer 2 is provided on the region of substrate 3 other than the central region, and the target 1 is provided on the central region of the substrate 3 and on the part of the electrically conducting layer 2 around the central region. Part of the electrically conducting layer 2 is covered with the target 1. Since the peripheral region of the substrate 3, which is not covered with the target 1, is covered with the electrically conducting layer 2, the secondary-X-ray transmissivity is higher at the peripheral region than at the central region.

Second Embodiment

This embodiment differs from the first embodiment in the shapes of the electron-passage forming member 4 and the electron passage 5 and is the same in commonalities other than the shapes of the electron-passage forming member 4 and the electron passage 5. The target unit can be any of the target units described in the first embodiment.

Figure 5A:
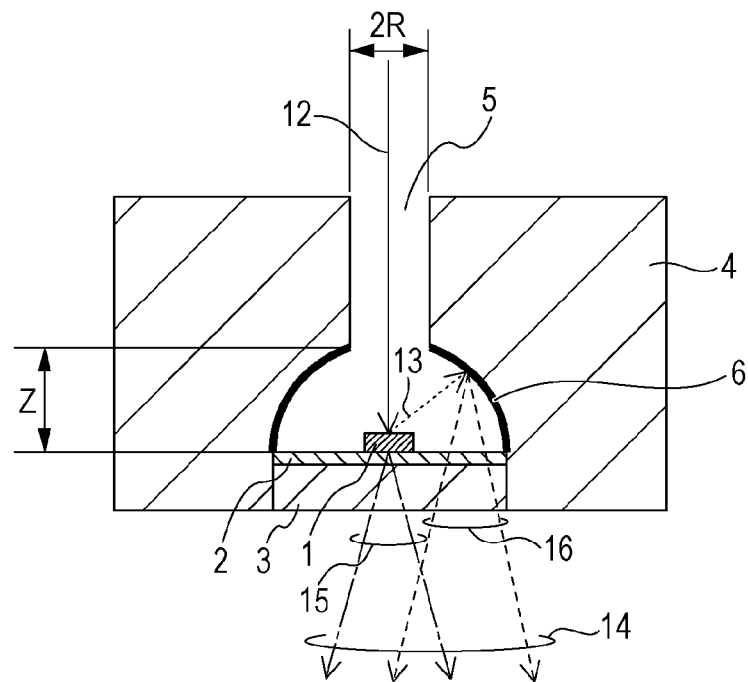
FIG. 5A is an enlarged view of the vicinity of the target of an X-ray tube according to a second embodiment of the present invention.

FIG. 5A is an enlarged view of the vicinity of the target 1 of this embodiment. The electron passage 5 whose both ends are open is formed by surrounding the periphery with the electron-passage forming member 4. The electron passage 5 has an upward convex arc cross-sectional shape in the direction perpendicular to the target 1 when the target 1 is assumed to be at the lower side. Furthermore, the inner wall surface of the enlarged-cross-sectional-area region of the electron passage 5 serves as the secondary-X-ray generation surface 6.

Since the cross-sectional shape of the secondary-X-ray generation surface 6 is an upward convex arc shape when the target 1 is assumed to be at the lower side, the X-rays 16 generated at the secondary-X-ray generation surface 6 are absorbed in the secondary-X-ray generation surface 6 at a low ratio, so that the amount of X-rays 16 extracted can be increased.

Third Embodiment

This embodiment differs from the first embodiment in the shapes of the electron-passage forming member 4 and the electron passage 5 and is the same in commonalities other than the shapes of the electron-passage forming member 4 and the electron passage 5. The target unit can be any of the target units described in the first embodiment.

Figure 5B:
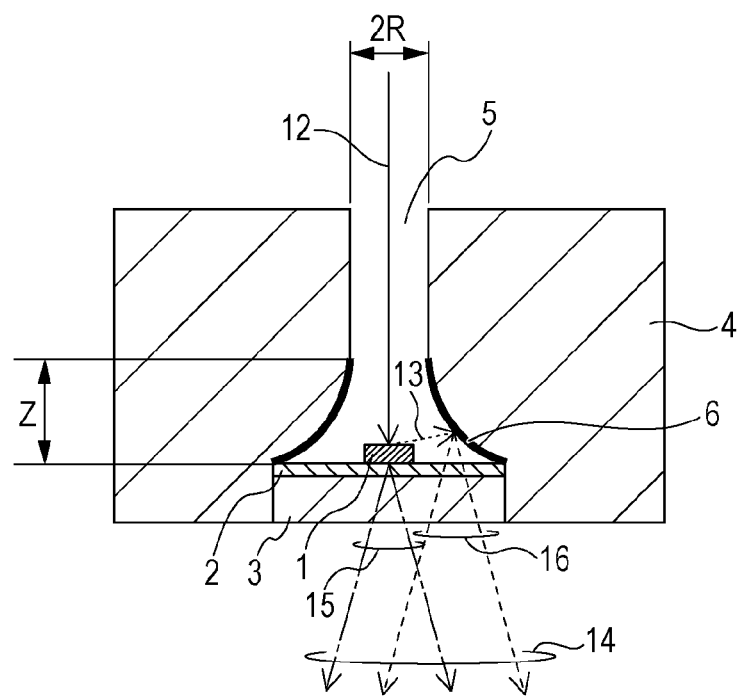
FIG. 5B is an enlarged view of the vicinity of the target of an X-ray tube according to a third embodiment of the present invention.

As shown in FIG. 5B, the electron passage 5 has a downward convex arc cross-sectional shape in the direction perpendicular to the target 1 when the target 1 is assumed to be at the lower side.

Since the cross-sectional shape of the secondary-X-ray generation surface 6 is a downward convex arc shape when the target 1 is assumed to be at the lower side, the X-rays 16 generated at the secondary-X-ray generation surface 6 is absorbed in the secondary-X-ray generation surface 6 at a low ratio, so that the amount of X-rays 16 extracted can be increased.

A preferable range of the area in which the secondary-X-ray generation surface 6 is formed is the same as that in the first embodiment.

The secondary-X-ray generation surface 6 and the target 1 may be disposed such that the secondary-X-ray generation surface 6 whose cross-sectional shape is a downward convex arc shape may be disposed over the target 1 so as to cover the surface thereof irradiated with the electrons 12.

Forth Embodiment

This embodiment differs from the first embodiment in the shapes of the electron-passage forming member 4 and the electron passage 5 and is the same in commonalities other than the shapes of the electron-passage forming member 4 and the electron passage 5. The target unit can be any of the target units described in the first embodiment.

Figure 6A:
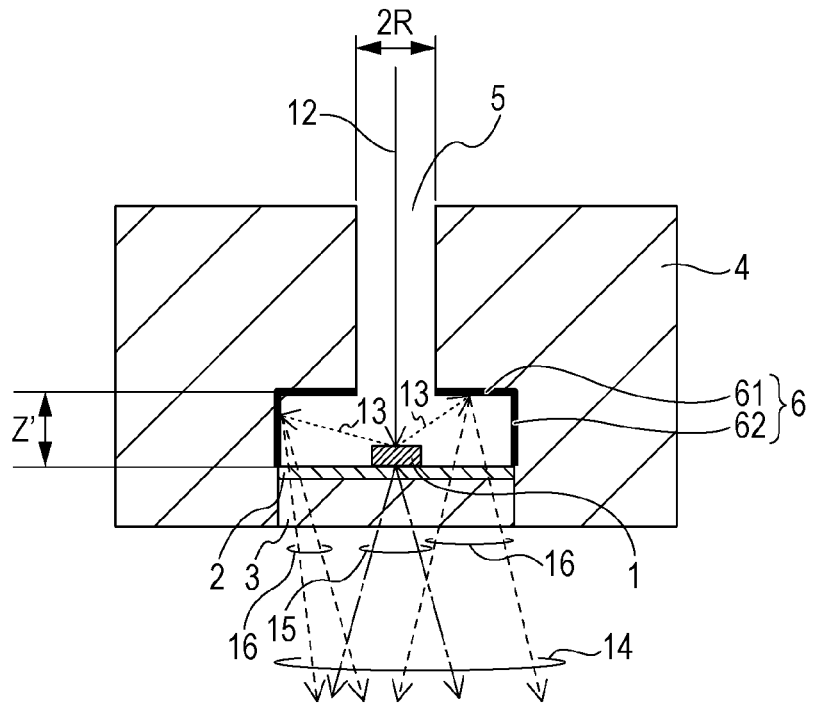
FIG. 6A is an enlarged view of the vicinity of the target of an X-ray tube according to a fourth embodiment of the present invention.

FIG. 6A is an enlarged view of the vicinity of the target 1 of this embodiment. The electron passage 5 whose both ends are open is formed by surrounding the periphery thereof with the electron-passage forming member 4. The cross-sectional area of at least the end of the electron passage 5 adjacent to the target 1 increases as compared with the opposite side to form a level difference. Furthermore, the inner wall surface of the enlarged-cross-sectional-area region of the electron passage 5 serves as the secondary-X-ray generation surface 6. It is sufficient that at least part of the inner wall surface of the increased-cross-sectional-area region of the electron passage 5 serve as the secondary-X-ray generation surface 6. In this embodiment, the secondary-X-ray generation surface 6 is constituted by a secondary-X-ray generation surface 61 parallel to the target 1 and a secondary-X-ray generation surface 62 perpendicular to the target 1. The secondary-X-ray generation surface 61 need not be parallel to the target 1, and the secondary-X-ray generation surface 62 need not be perpendicular to the target 1. The angle formed by the secondary-X-ray generation surface 61 and the secondary-X-ray generation surface 62 need not be 90°. The secondary-X-ray generation surface 6 may either be formed as part of the inner wall surface of the electron passage 5 or be formed, in the electron passage 5, of a different member from that of the electron passage 5.

Since the secondary-X-ray generation surface 61 is formed parallel to the target 1, the X-rays 16 generated at the secondary-X-ray generation surface 61 are absorbed in the secondary-X-ray generation surface 61 at a low ratio, so that the amount of X-rays 16 extracted can be increased.

A preferable range of the region in which the secondary-X-ray generation surface 6 is formed will be described. Since the collision density of the reflected electrons 13 becomes maximum at a location close to the target 1 (Z<1R), as shown in FIG. 4B, the secondary-X-ray generation surface 61 may be formed relatively close to the target 1. However, since the secondary-X-ray generation surface 62 also contributes to generation of X-rays, distance Z' is determined so that the total amount of X-rays 16 generated at the secondary-X-ray generation surface 61 and the secondary-X-ray generation surface 62 becomes the maximum.

The secondary-X-ray generation surface 6 and the target 1 may be disposed so that the secondary-X-ray generation surface 61 and the secondary-X-ray generation surface 62 are disposed over the target 1 so as to cover the surface thereof irradiated with the electrons 12. Furthermore, the secondary-X-ray generation surface 61, the secondary-X-ray generation surface 62, and the target 1 may be disposed so that the X-rays 15 that are generated when the target 1 is directly irradiated with the electrons 12 and the secondary X-rays 16 can be superposed one on another and can be extracted to the outside.

Fifth Embodiment

This embodiment differs from the fourth embodiment in part of the shapes of the electron-passage forming member 4 and the electron passage 5 and is the same in commonalities other than the shapes of the electron-passage forming member 4 and the electron passage 5. The target unit can be any of the target units described in the first embodiment.

Figure 6B:
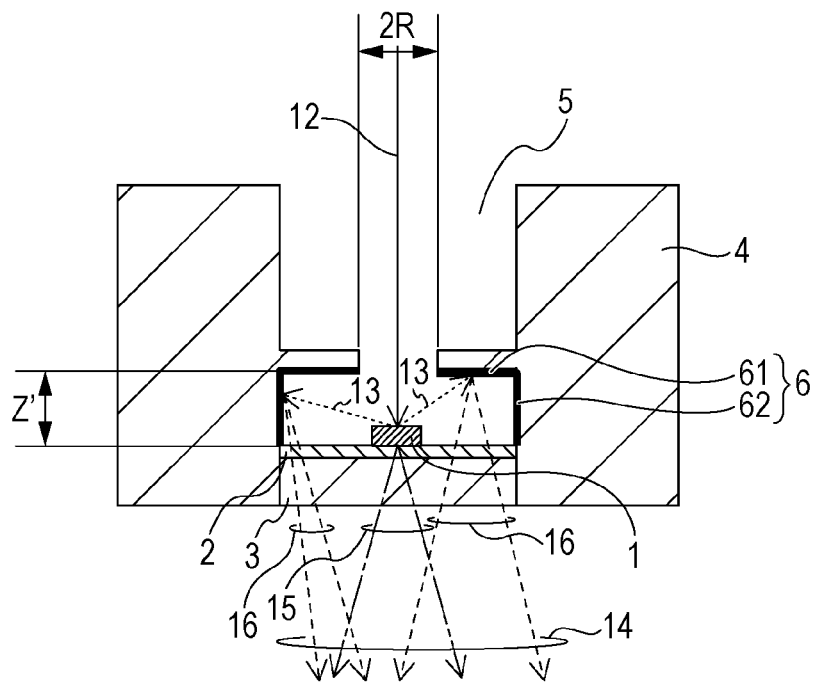
FIG. 6B is an enlarged view of the vicinity of the target of an X-ray tube according to a fifth embodiment of the present invention.

FIG. 6B is an enlarged view of the vicinity of the target 1 of this embodiment. The electron passage 5 whose both ends are open is formed by surrounding the periphery thereof with the electron-passage forming member 4. The electron passage 5 has a portion protruding from the inner wall surface of the electron passage 5 (hereinafter referred to as a protrusion) in an intermediate portion thereof. The protrusion may be ring-shaped as viewed from the target 1 side. The protrusion may either be formed of the same member as that of the electron passage 5 or be formed of a different member from the electron passage 5. The region of the electron passage 5 from the end adjacent to the target 1 to the protrusion serves as the secondary-X-ray generation surface 62, and the region of the protrusion opposing the target 1 serves as the secondary-X-ray generation surface 61. The secondary-X-ray generation surface 6 is constituted by the secondary-X-ray generation surface 61 and the secondary-X-ray generation surface 62. The secondary-X-ray generation surface 61 need not be parallel to the target 1, and the secondary-X-ray generation surface 62 need not be perpendicular to the target 1. The angle formed by the secondary-X-ray generation surface 61 and the secondary-X-ray generation surface 62 need not be 90°. The secondary-X-ray generation surface 6 may either be formed as part of the inner wall surface of the electron passage 5 or formed, in the electron passage 5, of a different member from that of the electron passage 5.

A preferable range of the region in which the secondary-X-ray generation surface 6 is formed is the same as that in the fourth embodiment. That is, the secondary-X-ray generation surface 61 may be formed relatively close to the target 1. However, since the secondary-X-ray generation surface 62 also contributes to generation of X-rays, distance Z' is determined so that the total amount of X-rays 16 generated at the secondary-X-ray generation surface 61 and the secondary-X-ray generation surface 62 becomes the maximum.

The secondary-X-ray generation surface 6 and the target 1 may be disposed so that the secondary-X-ray generation surface 61 and the secondary-X-ray generation surface 62 are disposed over the target 1 so as to cover the surface thereof irradiated with the electrons 12. Furthermore, the secondary-X-ray generation surface 61, the secondary-X-ray generation surface 62, and the target 1 may be disposed so that the X-rays 15 that are generated when the target 1 is directly irradiated with the electrons 12 and the secondary X-rays can be superposed on one another and can be extracted to the outside. With this disposition, the target 1 can be formed of a material that reflects 20% to 60% of the emitted electrons 12. Also with this disposition, the secondary-X-ray generation surface 6 may either be formed as part of the inner wall surface of the electron passage 5 or be formed, in the electron passage 5, of a different member from that of the electron passage 5.

As described above, in any of the foregoing embodiments, using the target units similar to that in the first embodiment allows the X-rays 16 generated due to the reflected electrons 13 generated at the target 1, in addition to the X-rays 15 generated at the target 1, can be efficiently extracted to the outside. Thus, the X-ray generation efficiency can be improved.

Sixth Embodiment

Figure 10:
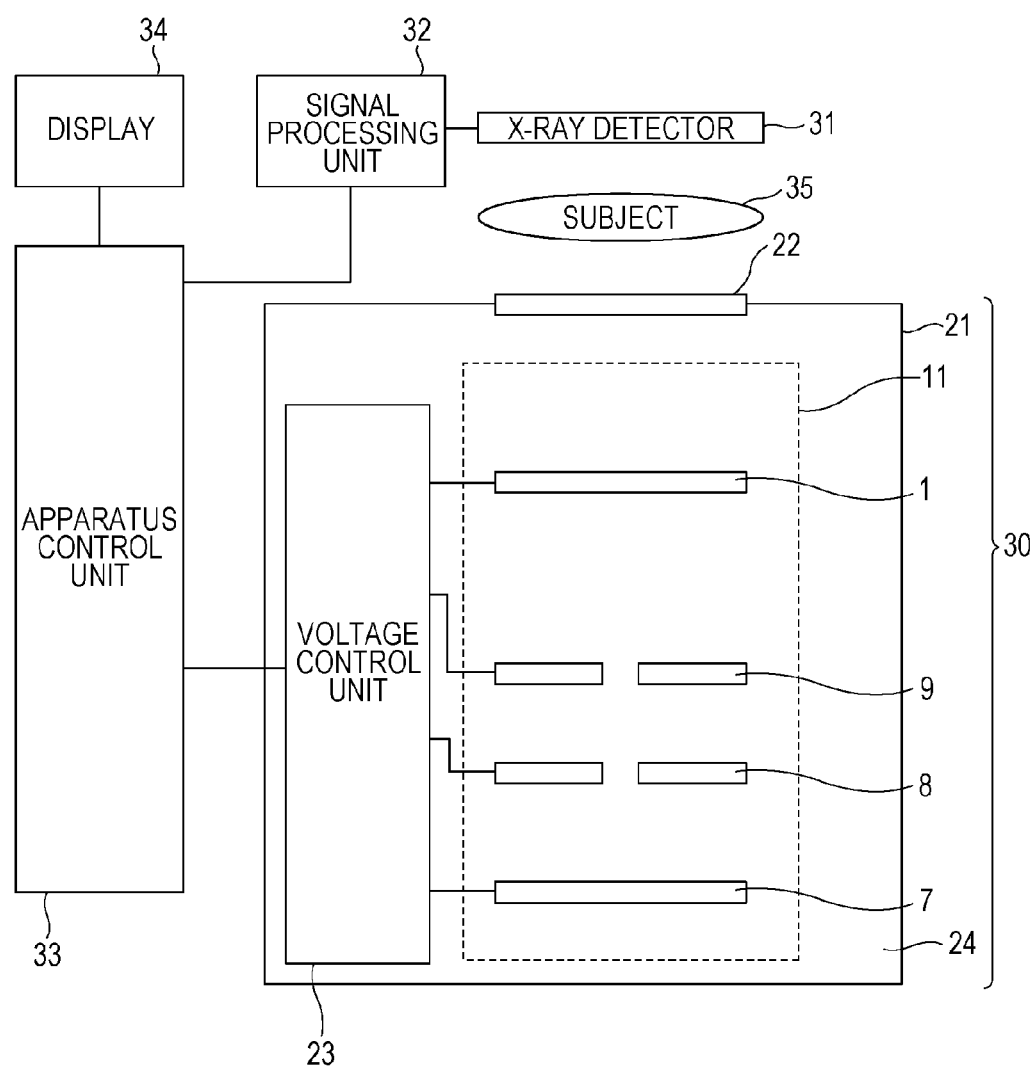
FIG. 10 is a block diagram of an X-ray imaging apparatus according to a sixth embodiment of the present invention.

FIG. 10 is a block diagram of an X-ray imaging apparatus of this embodiment.

First, an X-ray generator 30 equipped with the X-ray tube 11 described in the first to fifth embodiment will be described. The X-ray generator 30 accommodates the X-ray tube 11 in an envelope 21. The envelope 21 has an X-ray extraction window 22. X-rays generated from the X-ray tube 11 are radiated outside of the X-ray generator 30 through the X-ray extraction window 22.

The remaining space of the envelope 21 accommodating the X-ray tube 11 may be filled with an insulative medium 24. An example of the insulative medium 24 may be electrically insulating oil serving as an insulative medium and a cooling medium for the X-ray tube 11. Examples of the electrically insulating oil include mineral oil and silicone oil. Another available example of the insulative medium 24 includes fluorine electrically insulating liquid.

The envelope 21 may accommodate a voltage control unit 23 including a circuit board and an insulation transformer. If the voltage control unit 23 is provided, for example, a voltage signal is applied from the voltage control unit 23 to the X-ray tube 11, so that generation of X-rays can be controlled.

The X-ray imaging apparatus includes the X-ray generator 30, an X-ray detector 31, a signal processing unit 32, an apparatus control unit (hereinafter referred to as a control unit) 33, and a display 34. The X-ray detector 31 is connected to the control unit 33 via the signal processing unit 32. The control unit 33 is connected to the display 34 and the voltage control unit 23.

The control unit 33 controls the X-ray generator 30 and the X-ray detector 31 in a cooperative manner. X-rays generated from the X-ray generator 30 are detected by the X-ray detector 31 via a subject 35, and a fluoroscopic image of the subject 35 is acquired. The acquired fluoroscopic image is displayed on the display 34. The control unit 33 controls driving of the X-ray generator 30 and controls a voltage signal applied to the X-ray tube 11 via the voltage control unit 23.

Since this embodiment uses an X-ray generator whose X-ray generation efficacy is improved, a compact, high-resolution X-ray imaging apparatus can be provided.

The present invention will be described in detail below on the basis of examples and a comparative example.

Example 1

An X-ray generator of this example is the X-ray generator shown in FIG. 1A and includes the target unit in FIG. 1B and an anode constituted by the electron-passage forming member 4 having the electron passage 5 and the secondary-X-ray generation surface 6. First, a 0.1-μm titanium film was formed as the electrically conducting layer 2 over the entire surface (a surface on which electrons are to be incident) of a single-crystal diamond substrate 3 having a thickness of 1 mm and a diameter of 5 mm. Next, a 5-μm tungsten layer having a diameter of 1 mm was formed as the target 1 at the central region of the titanium layer on the diamond substrate 3 to form the target unit shown in FIG. 1B. Subsequently, the electron passage 5 having a diameter of 1.5 mm was formed in the electron-passage forming member 4 formed of tungsten. Thereafter, the substrate 3 and the electrically conducting layer 2 were brazed to the electron-passage forming member 4 to form the anode shown in FIG. 1B.

Example 2

An X-ray generator of this example is an X-ray generator including the target unit shown in FIG. 7A. This X-ray generator is the same as in Example 1, except for the target unit. First, a 5-μm tungsten layer having a diameter of 1 mm was formed as the target 1 at the central region of the surface of the single-crystal diamond substrate 3 having a thickness of 1 mm and a diameter of 5 mm. Next, a 0.1-μm titanium film was formed as the electrically conducting layer 2 on the entire surface of the diamond substrate 3, excluding the region where the tungsten layer was formed, to manufacture the target unit in FIG. 7A. Thereafter, an anode was formed as in Example 1.

Example 3

An X-ray generator of this example is an X-ray generator including the target unit shown in FIG. 7C. This X-ray generator is the same as in Example 1, except for the target unit. First, a 5-μm tungsten layer having a diameter of 1 mm was formed as the target 1 at the central region of the surface of a single-crystal diamond substrate 3 having a thickness of 1 mm and a diameter of 5 mm. Next, a 0.1-μm titanium film was formed as the electrically conducting layer 2 on the entire surface of the diamond substrate 3 including the region where the tungsten layer was formed to manufacture the target unit in FIG. 7C. Thereafter, an anode was formed as in Example 1.

Example 4

An X-ray generator of this example is an X-ray generator including the target unit shown in FIG. 7C. This X-ray generator differs from Example 3 in that tungsten was used as the electrically conducting layer 2. This example is the same as Example 1, except for the target unit. First, a 5-μm tungsten layer having a diameter of 1 mm was formed as the target 1 at the central region of the surface of the single-crystal diamond substrate 3 having a thickness of 1 mm and a diameter of 5 mm. Next, a 0.1-μm tungsten film was formed as the electrically conducting layer 2 on the entire surface of the diamond substrate 3 including the region where the tungsten layer was formed to manufacture the target unit in FIG. 7C. Thereafter, an anode was formed as in Example 1.

Example 5

An X-ray generator of this example is an X-ray generator including the target unit shown in FIG. 8A. This example is the same as Example 1, except for the target unit. First, a 5-μm tungsten layer having a diameter of 1 mm was formed as the target 1 at the central region of the surface of the single-crystal diamond substrate 3 having a thickness of 1 mm and a diameter of 5 mm. Next, a titanium film having a width of 0.3 mm and a thickness of 0.1 μm was formed on the surface of the diamond substrate 3 to the rim thereof, excluding the region where the tungsten layer was formed, in contact with the tungsten layer to manufacture the target unit in FIG. 8A. Thereafter, an anode was formed as in Example 1.

Example 6

An X-ray generator of this example is an X-ray generator including the target unit shown in FIG. 8C. This example is the same as Example 1, except for the target unit. First, a 5-μm tungsten layer having a diameter of 1 mm was formed as the target 1 at the central region of the surface of the single-crystal diamond substrate 3 having a thickness of 1 mm and a diameter of 5 mm to manufacture the target unit in FIG. 8C. The electrically conducting layer 2 was not provided. Thereafter, an anode was formed as in Example 1.

Comparison

As a comparative example, an X-ray generator including a target unit in which the target 1 is formed over the entire surface of the substrate 3. This X-ray generator is the same as in Example 1, except for the target unit. First, a 5-μm tungsten layer was formed as the target 1 over the entire surface of the single-crystal diamond substrate 3 having a thickness of 1 mm and a diameter of 5 mm to manufacture the target unit of the comparative example. Thereafter, an anode was formed as in Example 1.

Test Procedure

For comparison, the amounts of X-rays generated by the X-ray tubes 11 of the X-ray generators manufactured in the above examples and comparative example were measured by an ionization-chamber-type survey meter. The X-ray tube 11 was operated at voltages 60 kV and 100 kV, a current of 1 mA, and an operation time of 0.1 second. The measurement of the amounts of X-rays was performed, with the survey meter placed at a distance of 1 m from the target unit.

Measurement Results and Evaluation

Table 1 shows the measurement results of the amounts of X-rays extracted from the X-ray tube 11 in the above examples and comparative example according to the test procedure. Table 1 shows values of the amounts of X-rays at 60 kV and 100 kV in Examples 1 to 6 on the assumption that the amounts of X-rays at 60 kV and 100 kV in the comparative example are 100. The amounts of X-rays at 60 kV in Examples 1 to 6 are 114 to 118, and the amounts of X-rays at 100 kV in Examples 1 to 6 are 108 to 110. In any of Examples 1 to 6, a larger amount of X-rays can be obtained than that in the comparative example. The reason why the applied voltage of 60 kV provides a larger amount of X-rays than that at 100 kV may be that, the amount of X-rays absorbed is decreased by eliminating or decreasing the thickness of the film on a region other than a region directly irradiated with electron beams because the energy of the X-rays is low.

TABLE 1

|  | 60 kV | 100 kv |
| --- | --- | --- |
| Example 1 | 115 | 108 |
| Example 2 | 115 | 108 |
| Example 3 | 116 | 109 |
| Example 4 | 114 | 108 |
| Example 5 | 118 | 110 |
| Example 6 | 118 | 110 |
| Comparative example | 100 | 100 |

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2011-189112, filed Aug. 31, 2011 which is hereby incorporated by reference herein in its entirety.

REFERENCE SIGNS LIST 1 target
2 electrically conducting layer
3 substrate
4 electron-passage forming member
5 electron passage
6, 61, 62 secondary-X-ray generating section
14 to 16 X-rays
30 X-ray generator

The invention claimed is:

1. An X-ray generator comprising:
an anode including an electron passage formation member having an annular inner wall surface so as to define an electron passage hole;
an integrated target including a target layer and an insulating substrate supporting the target layer; and
an electron source facing the target layer so as to irradiate the target layer with electrons passing through the electron passage hole,
wherein the target layer is provided at a central region of the insulating substrate such that the integrated target includes a peripheral region and a periphery of the substrate is uncovered by the target layer,
wherein the electron passage formation member accommodates a secondary X-ray generating region at the annular inner wall surface that generates secondary X-rays by irradiation with electrons reflected from the target layer, and
wherein an angle θ formed by the secondary X-ray generating region and the target layer shows a relation $10°<θ<85°$ such that the electron passage formation member generates secondary X-rays in response to irradiation electron reflected from the target layer and at least a part of the secondary X-rays is transmitted outside of the X-ray generator through the peripheral region.

2. The X-ray generator according to claim 1, wherein the secondary-X-ray generating region is shaped so as to cover an above of a surface of the target layer irradiated with the electrons.

3. The X-ray generator according to claim 2, wherein a cross-sectional area of at least an end of the electron passage formation member adjacent to the target layer is larger than, and increases as compared with, an opposite side from the target layer, and at least part of the annular inner wall surface of the enlarged-cross-sectional area region serves as the secondary X-ray generating region.

4. The X-ray generator according to claim 3, wherein the increase in the cross-sectional area of at least the end of the electron passage formation member adjacent to the target layer has a level difference.

5. The X-ray generator according to claim 3, wherein the increase in the cross-sectional area of at least the end of the electron passage formation member adjacent to the target layer is a continuous increase.

6. The X-ray generator according to claim 3, wherein at least part of the X-rays generated by irradiation of the secondary X-ray generating region with the electrons reflected from the target layer passes through the target layer or the integrated target.

7. The X-ray generator according to claim 3, wherein the X-rays radiated to the outside through the peripheral region of the integrated target irradiated with the electrons are X-rays in which the X-rays generated by direct irradiation of the integrated target with the electrons and the X-rays generated by irradiation of the secondary X-ray generating region with the electrons reflected from the target layer are superimposed.

8. The X-ray generator according to claim 1, wherein the target layer reflects 20% to 60% of the irradiated electrons.

9. The X-ray generator according to claim 1, wherein an electrically conductive layer connected to the integrated target is provided at at least part of the periphery of the substrate, the periphery being not covered with the target layer.

10. The X-ray generator according to claim 9, wherein the electrically conductive layer is thinner than the target layer.

11. The X-ray generator according to claim 9, wherein the electrically conductive layer is formed of an element having a mass smaller than that of the target layer.

12. The X-ray generator according to claim 9, wherein the electrically conductive layer is provided on part of the periphery of the substrate, and another part of the periphery of the substrate is an exposed surface of the substrate.

13. The X-ray generator according to claim 1, wherein the secondary X-ray generating region is formed of the same material as that of the target layer.

14. An X-ray imaging apparatus comprising:
the X-ray generator according to claim 1;
an X-ray detector that detects X-rays generated from the X-ray generator and passing through a subject; and
a control unit that controls the X-ray generator and the X-ray detector in a cooperative manner.

15. The X-ray generator according to claim 1, wherein, the secondary X-ray generating region and the target layer are disposed so that both of primary X-rays generated by direct irradiation of the target layer with the electrons emitted from the electron source and secondary X-rays generated by irradiation of electrons reflected from the target layer are radiated to the outside.

16. The X-ray generator according to claim 1, wherein, the peripheral region shows higher transmittance for the secondary X-rays than the central region of the integrated target.

\* \* \* \* \*